United States Patent
Dugstad et al.

(10) Patent No.: US 6,221,337 B1
(45) Date of Patent: Apr. 24, 2001

(54) MICROBUBBLES SURROUNDED BY A MONOLAYER OF NEGATIVELY CHARGED PHOSPHOLIPIDS AS CONTRAST AGENTS

(75) Inventors: Harald Dugstad; Jo Klaveness; Pål Rongved; Roald Skurtveit; Jorunn Brænden, all of Oslo (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/136,410

(22) Filed: Aug. 19, 1998

Related U.S. Application Data (63) Continuation of application No. PCT/GB97/00459, filed on Feb. 19, 1997.

(30) Foreign Application Priority Data

| Feb. 19, 1996 | (GB) | 9603466 |
| Jun. 7, 1996 | (GB) | 9611894 |
| Dec. 11, 1996 | (GB) | 9625663 |

(51) Int. Cl.$^7$ .................. A61B 8/00; B32B 15/02
(52) U.S. Cl. ............... 424/9.52; 600/458; 428/402
(58) Field of Search ............... 424/9.52, 9.51, 424/9.5, 450, 489; 600/458, 441; 428/402; 516/11, 77

(56) References Cited

U.S. PATENT DOCUMENTS 5,531,980 * 7/1996 Schneider et al. ............ 424/9.52
5,585,112 * 12/1996 Unger et al. ............ 424/450

FOREIGN PATENT DOCUMENTS

| 0 494 615 | 7/1992 | (EP) . |
| 91 15244 | 10/1991 | (WO) . |
| 94 09829 | 5/1994 | (WO) . |
| 95 05854 | 3/1995 | (WO) . |

OTHER PUBLICATIONS

Schneider et al., Investigative Radiology, vol. 30, No. 8, 451–457 (1995).

Richardson et al., Journal of Nuclear Medicine, vol. 19, No. 9, 1049–1054 (1978).

Hnatowich et al., Journal of Nuclear Medicine, vol. 21, No. 7, 662–669 (1980).

* cited by examiner

Primary Examiner—Michael G. Hartley
(74) Attorney, Agent, or Firm—Bacon & Thomas (57) ABSTRACT

Microbubble dispersions stabilised by phospholipids predominantly comprising molecules which individually have an overall net charge exhibit advantageous stability, rendering them useful as efficacious contrast agents. An improved process for preparing microbubble-containing contrast agents is also disclosed, this comprising lyophilising an aqueous dispersion of gas microbubbles stabilised by one or more membrane-forming lipids to yield a dried product which may be reconstituted in an injectable carrier liquid to generate a microbubble-containing contrast agent.

6 Claims, 3 Drawing Sheets

MICROBUBBLES SURROUNDED BY A MONOLAYER OF NEGATIVELY CHARGED PHOSPHOLIPIDS AS CONTRAST AGENTS

This application is a continuation application of pending international application number PCT/GB97/00459 filed Feb. 19, 1997.

This invention relates to novel gas-containing contrast agents of use in diagnostic imaging, more particularly to such contrast agents comprising phospholipid-stabilised gas microbubbles and to a novel method for the preparation of gas-containing contrast agents.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Gas-containing contrast media are also known to be effective in magnetic resonance (MR) imaging, e.g. as susceptibility contrast agents which will act to reduce MR signal intensity. oxygen-containing contrast media also represent potentially useful paramagnetic MR contrast agents.

Furthermore, in the field of X-ray imaging it has been observed that gases such as carbon dioxide may be used as negative oral contrast agents or intravascular contrast agents.

The use of radioactive gases, e.g. radioactive isotopes of inert gases such as xenon, has also been proposed in scintigraphy, for example for blood pool imaging.

Initial studies involving free gas bubbles generated in vivo by intracardiac injection of physiologically acceptable substances have demonstrated the potential efficiency of such bubbles as contrast agents in echography; such techniques are severely limited in practice, however, by the short lifetime of the free bubbles. Interest has accordingly been shown in methods of stabilising gas bubbles for echocardiography and other ultrasonic studies, for example using emulsifiers, oils, thickeners or sugars, or by entraining or encapsulating the gas or a precursor therefor in a variety of systems, e.g. as porous gas-containing microparticles or as encapsulated gas microbubbles.

There is a body of prior art regarding use of phospholipids as components of gas-containing ultrasound contrast agents. Thus, for example, the use as ultrasound contrast media of phospholipid liposomes in which a lipid bilayer surrounds a confined composition including a gas or gas precursor is disclosed in U.S. Pat. No. 4,900,540. The encapsulated material is typically a gas precursor such as aqueous sodium bicarbonate, which is said to generate carbon dioxide following administration through exposure to body pH. The cores of the resulting liposomes will therefore tend to comprise liquid containing extremely small microbubbles of gas which will exhibit only limited echogenicity by virtue of their small size.

WO-A-9115244 discloses ultrasound contrast media comprising microbubbles of air or other gas formed in a suspension of liquid-filled liposomes, the liposomes apparently stabilising the microbubbles. Such systems are differentiated from those of the above-mentioned U.S. Pat. No. 4,900,540 in which the air or other gas is inside the liposomes.

WO-A-9211873 describes aqueous preparations designed to absorb and stabilise microbubbles and thereby serve as ultrasound contrast agents, the compositions comprising polyoxyethylene/polyoxypropylene polymers and negatively charged phospholipids. The weight ratio of polymer to phospholipid is typically about 3:1.

Ultrasound contrast agents comprising gas-filled liposomes, i.e. liposomes which are substantially devoid of liquid in the interior thereof, and their preparation by a vacuum drying gas instillation method are described in WO-A-9222247. The preparation of such gas-filled liposomes by a gel state shaking gas instillation method is described in WO-A-9428780. A report on gas-filled lipid bilayers composed of dipalmitoylphosphatidyl-choline as ultrasound contrast agents is presented by Unger et al. in Investigative Radiology 29, Supplement 2, S134–S136 (1994).

WO-A-9409829 discloses injectable suspensions of gas microbubbles in an aqueous carrier liquid comprising at least one phospholipid stabiliser, the concentration of phospholipids in the carrier being less than 0.01% w/w but equal to or above the amount at which phospholipid molecules are present solely at the gas microbubble-liquid interface. The amount of phospholipid may therefore be as low as that necessary for formation of a single monolayer of surfactant around the gas microbubbles, the resulting film-like structure stabilising the bubbles against collapse or coalescence. Microbubbles with a liposome-like surfactant bilayer are to said not to be obtained when such low phospholipid concentrations are used.

A further body of prior art concerns selection of gases for gas microbubble-containing ultrasound contrast media in order to enhance properties such as their stability and duration of echogenic effect. Thus, for example, WO-A-9305819 proposes use of free microbubbles of gases having a coefficient Q greater than 5 where $$Q=4.0 \times 10^{-7} \times \rho/C_s D$$

(where $\rho$ is the density of the gas in $kg \cdot m^{-3}$, $C_s$ is the water solubility of the gas in $moles \cdot l^{-1}$ and D,is the diffusivity of the gas in solution in $cm^3 \cdot sec^{-1}$). An extensive list of gases said to fulfill this requirement is presented.

EP-A-0554213 suggests that one may impart resistance against collapse under pressure to gas-filled microvesicles by introduction thereto of at least one gas whose solubility in water, expressed in litres of gas/litres of water under standard conditions, divided by the square root of its molecular weight does not exceed 0.003. Preferred gases are said to include sulphur hexafluoride, selenium hexafluoride and various Freonse. Such gases may, inter alia, be used in phospholipid-containing compositions of the type described in the above-mentioned WO-A-9215244.

Schneider et al. in Investigative Radiology 30(8), pp. 451–457 (1995) describe a new ultrasonographic contrast agent based on sulphur hexafluoride-filled microbubbles apparently stabilised by a combination of polyethyleneglycol 4000 and a mixture of the phospholipids distearoylphosphatidylcholine and dipalmitoylphosphatidylglycerol. The use of sulphur hexafluoride rather than air is said to provide improved resistance to pressure increases such as occur in the left heart during systole.

WO-A-9503835 proposes use of microbubbles containing a gas mixture the composition of which is based on considerations of gas partial pressures both inside and outside the microbubbles, so as to take account of osmotic effects on microbubble size. Representative mixtures comprise a gas having a low apour pressure and limited solubility in blood or serum (e.g. a fluorocarbon) in combination with another gas hich is more rapidly exchanged with gases present in normal blood or serum (e.g. nitrogen, oxygen, carbon dioxide or mixtures thereof).

WO-A-9516467 suggests use of ultrasound contrast media containing a mixture of gases A and B, where gas B is present in an amount of 0.5–41% v/v, has a molecular weight greater than 80 daltons and has aqueous solubility below 0.0283 ml/ml water under standard conditions, the balance of the mixture being gas A. Representative gases A include air, oxygen, nitrogen, carbon dioxide and mixtures thereof. Representative gases B include fluorine-containing gases such as sulphur hexafluoride and various perfluorinated hydrocarbons. Preferred stabilisers in such contrast media include phospholipids.

Phospholipids said to be useful in prior art contrast agents include lecithins (i.e. phosphatidylcholines), for example natural lecithins such as egg yolk lecithin or soya bean lecithin and synthetic or semisynthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; cardiolipins; sphingomyelins; mixtures of any of the foregoing and mixtures with other lipids such as cholesterol. Lecithin derivatives generally appear to be the most commonly used phospholipids, possibly by virtue of their ready availability from natural sources. The use of additives such as cholesterol in amounts of up to 50% w/w is disclosed in WO-A-9115244 and WO-A-30 9409829, whilst the incorporation of at least a small amount (e.g. ca. 1 mole %) of negatively charged lipid (e.g. phosphatidylserine or a fatty acid) to enhance stability is suggested in WO-A-9222247. A preferred phospholipid composition according to WO-A-9428780 comprises dipalmitoylphosphatidylcholine, polyethylene-glycol 5000-substituted dipalmitoylphosphatidylethanolamine and dipalmitoylphosphatidic acid in molar proportions of about 87:8:5. Typical mixed phoapholipid compositions according to WO-A-9409829 and WO-A-9516467 comprise diarachidoylphosphatidylcholine and dipalmitoylphosphatidic acid in weight proportions of about 100:4, although the latter specification also exemplifies use of equal amounts by weight of distearoylphosphatidylcholine and dipalmitoylphosphatidylglycerol.

It will be apparent from the foregoing that in existing phospholipid-containing microbubble suspensions proposed for use as contrast media, at least 50% of the phospholipid content comprises neutral phospholipids such as lecithins. Most commonly only a minor proportion, e.g. ca. 5%, of charged phospholipids is present.

The present invention is based on the finding that the use of predominantly charged phospholipids as essentially the sole amphiphilic component of microbubble-containing contrast agents may convey valuable and unexpected benefits in terms of parameters such as product stability and acoustic properties. Whilst we do not wish to be bound by theoretical considerations it is believed that electrostatic repulsion between charged phospholipid membranes encourages the formation of stable and stabilising monolayers at microbubble-carrier liquid interfaces; the flexibility and deformability of such thin membranes will enhance the echogenicity of products according to the invention relative to gas-filled liposomes comprising one or more lipid bilayers.

We have also found that the use of charged phospholipids may enable the provision of microbubble contrast agents with advantageous properties regarding, for example, stability, dispersibility and resistance to coalescence without recourse to additives such as further surfactants and/or viscosity enhancers, thereby ensuring that the number of components administered to the body of a subject upon injection of the contrast agents is kept to a minimum. Thus, for example, the charged surfaces of the microbubbles may minimise or prevent their aggregation as a result of electrostatic repulsion.

Thus, according to one embodiment of the present invention, there is provided a contrast agent for use in diagnostic studies comprising a suspension in an injectable aqueous carrier liquid of gas microbubbles stabilised by phospholipid-containing amphiphilic material characterised in that said amphiphilic material consists essentially of phospholipid predominantly comprising molecules with net charges.

Desirably at least 75%, preferably substantially all of the phospholipid material in the contrast agents of the invention consists of molecules bearing a net overall charge under conditions of preparation and/or use, which charge may be positive or, more preferably, negative. Representative positively charged phospholipids include esters of phosphatidic acids such as dipalmitoylphosphatidic acid or distearoylphosphatidic acid with aminoalcohols such as hydroxyethylenediamine. Examples of negatively charged phospholipids include naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and cardiolipins. The fatty acyl groups of such phospholipids will typically each contain about 14–22 carbon atoms, for exmple -as in palmitoyl and stearoyl groups. Lyso forms of such charged phospholipids are also useful in accordance with the invention, the term "lyso" denoting phospholipids containing only one fatty acyl group, this preferably being ester-linked to the 1-position carbon atom of the glyceryl moiety. Such lyso forms of charged phospholipids may advantageously be used in admixture with charged phospholipids containing two fatty acyl groups.

Phosphatidylserines represent particularly preferred phospholipids of use in contrast agents according to the invention and preferably constitute a substantial part, e.g. at least 80% of the initial phospholipid content thereof, for example 85–92%, although this may subsequently be reduced somewhat, e.g. to ca. 70%, in subsequent processing such as heat sterilisation. It will be appreciated that such processing may lead to formation of non-phospholipid degradation products such as free fatty acids, e.g. at levels of up to 10%; references herein to amphiphilic material consisting essentially of phospholipid are to be construed as embracing phospholipids containing such free fatty acids. While we do not wish to be bound by theoretical considerations, it may be that ionic bridging between the carboxyl and amino groups of adjacent serine moieties contributes to the stability of phosphatidylserine-containing systems, for example as evidenced by their good pressure stability. Preferred phosphatidylserines include saturated (e.g. hydrogenated or synthetic) natural phosphatidylserine and synthetic or semi-synthetic dialkanoylphosphatidylserines such as distearoylphosphatidylserine, dipalmitoylphosphatidylserine and diarachidoylphosphatidylserine.

An important advantage of the use of such phosphatidylserine-based contrast agents is that the body recognises aged red blood cells and platelets by high concentrations of phosphatidylserine on their surface and so may eliminate such contrast agents from the blood stream in a manner similar to the elimination of red blood cells.

Furthermore, since the surface of such contrast agents may be registered as endogenous by the body, they may avoid induction of adverse systemic ide effects such as haemodynamic effects and other naphylactic reactions which may accompany administration of some liposome preparations (see e.g. WO-A-9512386). In support of this, no acute toxic effects such as changes in blood pressure or heart rate have been observed in animal tests on dogs injected with intravenous boluses of contrast agents according to the invention at doses of up to ten times a normal imaging dose.

Any biocompatible gas may be employed in the contrast agents of the invention, it being appreciated that the term "gas" as used herein includes any substances (including mixtures) substantially or completely in gaseous (including vapour) form at the normal human body temperature of 37° C. The gas may thus, for example, comprise air; nitrogen; oxygen; is carbon dioxide; hydrogen; nitrous oxide; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. At least some of the halogen atoms in halogenated gases advantageously are fluorine atoms. Thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane and perfluorocarbons, e.g. perfluoroalkanes such as perfluoromethane, perfluoroethane, perfluoropropanes, perfluorobutanes (e.g. perfluoro-n-butane, optionally in admixture with other isomers such as perfluoroisobutane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane. Other halogenated gases include fluorinated, e.g. is perfluorinated, ketones such as perfluoroacetone and fluorinated, e.g. perfluorinated, ethers such as perfluorodiethyl ether.

It may be advantageous in contrast agents of the invention to employ fluorinated gases such as sulphur fluorides or fluorocarbons (e.g. perfluorocarbons) which are known to form particularly stable microbubble suspensions (see, for example, the article by Schneider et al. referred to above). Gas mixtures based on considerations of partial pressures both inside and outside the microbubbles and consequent osmotic effects on microbubble size, e.g. as described in WO-A-9503835, may if desired be employed, for example a mixture of a relatively blood-soluble gas such as nitrogen or air and a relatively blood-insoluble gas such as a perfluorocarbon.

We have found, however, that contrast agents of the invention, for example comprising microbubbles of a perfluoroalkane such as perfluorobutane stabilised by phosphatidylserine, are surprisingly stable in size following intravenous administration to a subject, and do not exhibit the previously described tendency of microbubbles of such gases to grow uncontrollably as a result of inward diffusion of blood gases such as oxygen, nitrogen and carbon dioxide, instead rapidly reaching a maximum size beyond which further growth is not observed. This avoidance of unlimited size increases which could lead to undesirable and potentially highly dangerous blocking of blood vessel capilliaries is a major advantage of contrast agents according to the invention.

Contrast agents of the invention comprising perfluoroalkanes such as perfluorobutane have also been found to exhibit surprisingly high stability under pressures similar to those typically encountered in vivo, for example showing substantially complete (e.g. at least 90%) recovery to normal size distribution and echogenic properties after exposure to overpressures (e.g. of air) of up to 300 mm Hg for 90 seconds.

The contrast agents of the invention may be used in a variety of diagnostic imaging techniques, including scintigraphy, light imaging, ultrasound, MR and X-ray (including soft X-ray) imaging. Their use in diagnostic ultrasound imaging and in MR imaging, e.g. as susceptibility contrast agents, constitute preferred features of the invention. A variety of imaging techniques may be employed in ultrasound applications, for example including fundamental and harmonic B-mode imaging and fundamental and harmonic Doppler imaging; if desired three-dimensional imaging techniques may be used. The contrast agent may also be used in ultrasound imaging methods based on correlation techniques, for example as described in U.S. Pat. No. 5,601,085 and International Patent Application No. PCT/GB96/02413.

In vivo ultrasound tests in dogs have shown that contrast agents according to the invention may produce an increase in backscattered signal intensity from the myocardium of 15–25 dB following intravenous injection of doses as low as 1–20 nl microbubbles/kg body weight. Signals may be observed at even lower doses using more sensitive techniques such as colour Doppler or Doppler-derived techniques, e.g. amplitude based Doppler or non-linear techniques such as are described by Tucker et al. in Lancet (1968) p. 1253, by Miller in Ultrasonics (1981) pp. 217–224, and by Newhouse et al. in J. Acoust. Soc. Am. 75, pp. 1473–1477 (1984). At these low doses attenuation in blood-filled compartments such as the heart chambers has been found to be sufficiently low to permit visualisation of regions of interest in the myocardial vasculature. Tests have also shown such intravenously injected contrast agents to be distributed throughout the whole blood pool, thereby enhancing the echogenicity of all vascularised tissues, and to be recirculated. They have also been found useful as general Doppler signal enhancement aids, and may additionally be useful in ultrasound computed tomography and in physiologically triggered or intermittent imaging.

For ultrasound applications such as echocardiography, in order to permit free passage through the pulmonary system and to achieve resonance with the preferred imaging frequencies of about 0.1–15 MHz, it may be convenient to employ microbubbles having an average size of 0.1–10 $\mu$m, e.g. 1–7 $\mu$m. We have found that contrast agents according to the invention may be produced with a very narrow size distribution for the microbubble dispersion within the range preferred for echocardiography, thereby greatly enhancing their echogenicity as well as their safety in vivo, and rendering the contrast agents of particular advantage in applications such as blood pressure measurements, blood flow tracing and ultrasound tomography. Thus, for example, products in which over 90% (e.g. at least 95%, preferably at least 98%) of the microbubbles have diameters in the range 1–7 μm and less than 5% (e.g. not more than 3%, preferably not more than 2%) of the microbubbles have diameters above 7 μm may readily be prepared.

In ultrasound applications the contrast agents of the invention may, for example, be administered in doses such that the amount of phospholipid injected is in the range 0.1–10 μg/kg body weight, e.g. 1–5 μg/kg in the case of fundamental B-mode imaging. It will be appreciated that the use of such low levels of phospholipid is of substantial advantage in minimising possible toxic side effects. Furthermore, the low levels of phospholipids present in effective doses may permit dosage increases to prolong observation times without adverse effects.

The overall concentration of phospholipid in injectable forms of contrast agents according to the invention may conveniently be in the range 0.01–2% w/w, for example 0.2–0.8% w/w, advantageously about 0.5% w/w.

In general we have found it unnecessary to incorporate additives such as emulsifying agents and/or viscosity enhancers which are commonly employed in many existing contrast agent formulations into contrast agents of the invention. As noted above this is of advantage in keeping to a minimum the number of components administered to the body of a subject and ensuring that the viscosity of the contrast agents is as low as possible. Since preparation of the contrast agents typically involves a freeze drying step as discussed in further detail hereinafter it may, however, be advantageous to include one or more agents with cryoprotective and/or lyoprotective effect and/or one or more bulking agents, for example an alcohol, e.g. an aliphatic alcohol such as t-butanol; a polyol such as glycerol; an aminoacid such as glycine; a carbohydrate, e.g. a sugar such as sucrose, mannitol, trehalose, glucose, lactose or a cyclodextrin, or a polysaccharide such as dextran; or a polyglycol such as polyethylene glycol. A substantial list of agents with cryoprotective and/or lyoprotective effects is given in Acta Pharm. Technol. 34(3), pp. 129–139 (1988), the contents of which are incorporated herein by reference. The use of physiologically well-tolerated sugars such as sucrose, e.g. in an amount such as to render the product isotonic or somewhat hypertonic, is preferred.

Prior art microbubble-containing contrast agents, for example as described in WO-A-9409829, are typically prepared by contacting powdered surfactant, e.g. freeze-dried preformed liposomes or freeze-dried or spray-dried phospholipid solutions, with air or other gas and then with aqueous carrier, agitating to generate a microbubble suspension which must then be administered shortly after its preparation. Such processes, however, suffer the disadvantages that substantial agitational energy must be imparted to generate the required dispersion and that the size and size distribution of the microbubbles are dependent on the amount of energy applied and so cannot in practice be controlled.

We have now found that contrast agents according to the invention may advantageously be prepared by generating a gas microbubble dispersion in an appropriate phospholipid-containing aqueous medium, which may if desired previously have been autoclaved or otherwise sterilised, and thereafter subjecting the dispersion to lyophilisation to yield a dried reconstitutable product. Such products, e.g. comprising the lyophilised residue of a suspension of gas microbubbles in an amphiphilic material-containing aqueous medium wherein the amphiphilic material consists essentially of phospholipid predominantly comprising molecules with net charges, constitute a further feature of the present invention. Where the dried product contains one or more cryoprotective and/or lyoprotective agents it may, for example, comprise a microbubble-releasing cryoprotectant and/or lyoprotectant (e.g. carbohydrate) matrix containing gas-filled substantially spherical cavities or vacuoles surrounded by one or more layers of the amphiphilic material.

More particularly we have found that dried products so prepared are especially readily reconstitutable in aqueous media such as water, an aqueous solution such as saline (which may advantageously be balanced so that the final product for injection is not hypotonic), or an aqueous solution of one or more tonicity-adjusting substances such as salts (e.g. of plasma cations with physiologically tolerable counterions), or sugars, sugar alcohols, glycols and other non-ionic polyol materials (e.g. glucose, sucrose, sorbitol, mannitol, glycerol, polyethylene glycols, propylene glycols and the like) requiring only minimal agitation such as may, for example, be provided by gentle hand-shaking. The size of the microbubbles so generated is consistently reproducible and in practice is independent of the amount of agitational energy applied, being determined by the size of the microbubbles formed in the initial microbubble dispersion, this size parameter surprisingly being substantially maintained in the lyophilised and reconstituted product. Thus, since the size of the microbubbles in the initial dispersion may readily be controlled by process parameters such as the method, speed and duration of agitation, the final microbubble size may readily be controlled.

Lyophilised products according to the invention have proved to be storage stable for several months under ambient conditions. The microbubble dispersions generated upon reconstitution in water or an aqueous solution may be stable for at least 12 hours, permitting considerable flexibility as to when the dried product is reconstituted prior to injection.

The above-described process for the preparation of contrast agents according to the invention is generally applicable to the preparation of contrast agents comprising suspensions in an injectable aqueous. carrier liquid of gas microbubbles stabilised by membrane-forming lipids, including both neutral and charged lipids (e.g. phospholipids) as well as mixtures thereof. Such a process, comprising the steps:

i) generating a dispersion of gas microbubbles in an aqueous medium containing a membrane-forming lipid;

ii) lyophilising the thus-obtained lipid-stabilised gas dispersion to yield a dried lipid-containing product; and iii) reconstituting the said dried product in an injectable aqueous carrier liquid, constitutes a further feature of the present invention, as does a reconstitutable dried product obtainable in accordance with steps (i) and (ii) of this process, for example a product comprising a microbubble-releasing matrix (e.g. of cryoprotectant/lyoprotectant) containing gas-filled substantially spherical cavities or vacuoles surrounded by layers of membrane-forming lipid material.

Step (i) may, for example, be effected by subjecting the lipid-containing aqueous medium to any appropriate emulsion-generating technique, for example sonication, shaking, high pressure homogenisation, high speed stirring or high shear mixing, e.g. using a rotor-stator homogeniser, in the presence of the selected gas. The aqueous medium may, if desired, contain additives which serve as viscosity enhancers and/or as solubility aids for the lipid, such as alcohols or polyols, e.g. glycerol and/or propylene glycol.

The gas employed in the emulsification step need not be that desired in the final product. Thus most of this gas content may be removed during the subsequent lyophilisation step and residual gas may be removed by evacuation of the dried product, to which an atmosphere of the desired end product gas may then be applied. The emulsification gas may therefore be selected purely to optimise the emulsification process parameters, without regard to end product considerations. We have found emulsification in the presence of a sulphur fluoride such as sulphur hexafluoride or a fluorinated hydrocarbon gas such as a perfluoroalkane or perfluorocycloalkane, preferably containing 4 or 5 carbon atoms, to be particularly advantageous in terms of ultimately yielding end products with consistent and narrowly distributed microbubble sizes.

The emulsification is conveniently effected at about ambient temperature, e.g. at ca. 25±10° C. It may be necessary initially to heat the aqueous medium to facilitate hydration and thus dispersion of the phospholipid and then allow it to equilibrate to ambient temperature prior to emulsification.

Gas dispersions obtainable according to step (i), especially aqueous dispersions of gas microbubbles is stabilised by amphiphilic material consisting essentially of phospholipid predominantly comprising molecules with net charges, constitute a feature of the invention. Certain such dispersions are disclosed in our International Patent Publication No. WO-A-9640275 as intermediates for use in the preparation of diagnostic contrast agents comprising microbubbles of gas stabilised by one or more membrane-forming lipids crosslinked or polymerised in the hydrophilic portion thereof. These intermediate dispersions, in which the amphiphilic material comprises dipalmitoylphosphatidylserine, more particularly in the form of its sodium salt, either alone or in combination with dipalmitoylphosphatidylcholine, and the gas is a mixture of air with perfluoropentane, a mixture of air with perfluorohexane or a mixture of perfluorobutane with perfluorohexane, are hereby disclaimed.

It will be appreciated that, by virtue of being intermediates, these dispersions will not have been prepared in sterile, physiologically acceptable form, whereas gas dispersions obtainable according to step (i) in accordance with the present invention will be prepared in sterile, physiologically acceptable form (e.g. using sterile, pyrogen-free water or saline as the aqueous carrier liquid) if they are intended for use as contrast agents per se.

Dispersions produced according to step (i) may advantageously be subjected to one or more washing steps prior to contrast agent use or to lyophilisation step (ii), in order to separate and remove additives such as viscosity enhancers and solubility aids, as well as unwanted material such as non-gas-containing colloidal particles and undersized and/or oversized microbubbles; the washed microbubble dispersions so obtained constitute a feature of the invention. Such washing may be effected in per se known manner, the microbubbles being separated using techniques such as flotation or centrifugation. The ability to remove additives in this way and also to obtain microbubble dispersions with a particularly narrow size distribution represent important advantages of the process of the invention especially since, as noted above, the resulting size distribution is substantially retained after lyophilisation and reconstitution. Accordingly it is particularly preferred to use a process comprising gas dispersion, washing/separation, lyophilisation and reconstitution steps.

Size-fractionated microbubble dispersions may be prepared wherein at least 90% of the microbubbles have sizes within a 2 μm range, the microbubbles preferably having a volume mean diameter within the range 2–5 μm. Such dispersions and frozen and lyophilised products derived therefrom, e.g. as described hereinafter, represent further features of the invention.

Where one or more cryoprotective and/or lyoprotective agents are employed these may advantageously be added after the washing steps, prior to lyophilisation.

Lyophilisation of the gas dispersion may, for example, be effected by initially freezing it and thereafter lyophilising the frozen gas dispersion, for example in per se generally known manner. Such frozen gas dispersions, i.e. frozen microbubble-releasing aqueous dispersions comprising gas microbubbles stabilised by amphiphilic material consisting essentially of phospholipid predominantly comprising molecules which individually have an overall net charge, constitute a further feature of the invention. The microbubbles may preferably be size fractionated prior to freezing, the released microbubbles preferably having a volume mean diameter within the range 2–5 μm. Such products may be stored frozen and thawed when desired, e.g. by simple warming and/or by addition of a carrier liquid, to regenerate microbubble dispersions useful as contrast agents in accordance with the invention.

Since the dried product will normally be reconstituted in accordance with step (iii) above prior to administration, the gas dispersion may advantageously be filled into sealable vials prior to lyophilisation so as to give vials each containing an appropriate amount, e.g. a single dosage unit, of lyophilised dried product for reconstitution into an injectable form. By lyophilising the gas dispersion in individual vials rather than in bulk, handling of the delicate honeycomb-like structure of the lyophilised product and the risk of at least partially degrading this structure are avoided. Following lyophilisation and any optional further evacuation of gas and introduction into the headspace of gas desired to be present as microbubbles in the ultimately formulated contrast agent, the vials may be sealed with an appropriate closure. It will be appreciated that the ability to select the end product gas content, coupled with the ability independently to control the end product microbubble size by selection of appropriate process parameters during the initial dispersion step and any ensuing washing/separation step, enable the independent selection of microbubble size and gas content, thereby permitting the products to be matched to particular applications.

In general the frozen gas dispersion or the dried product from step (ii), e.g. after any necessary and/or desired supplementation or exchange of gas content, may be reconstituted by addition of an appropriate sterile aqueous injectable carrier liquid such as sterile pyrogen-free water for injection, an aqueous solution such as saline (which may advantageously be balanced so that the final product for injection is not hypotonic), or an aqueous solution of one or more tonicity-adjusting substances (e.g. as hereinbefore described). Where the dried product is contained in a vial this is conveniently sealed with a septum through which the carrier liquid may be injected using an optionally prefilled syringe; alternatively the dried product and carrier liquid may be supplied together in a dual chamber device such as a dual chamber syringe. It may be advantageous to mix or gently shake the product following reconstitution. However, as noted above, in the stabilised contrast agents according to the invention the size of the gas microbubbles may be substantially independent of the amount of agitational energy applied to the reconstituted dried product. Accordingly no more than gentle hand-shaking may be required to give reproducible products with consistent microbubble size.

The following non-limitative Examples serve to illustrate the invention.

EXAMPLE 1

Effects of Relative Amounts of Charged Phospholipids

Dispersions of microbubbles stabilised by different phospholipids or phospholipid mixtures were made according to the general procedure described below, using the process parameters given in Table 1.1 below.

Solutions of the selected phospholipids or phospholipid mixtures in water containing 5.4% (w/w) of a mixture of propylene glycol and glycerol (3:10 w/w) giving a phospholipid concentration of 2–5 mg/ml were prepared (for phosphatidylethanolamine the water was adjusted to pH=10.5 with sodium hydroxide), the phospholipids being hydrated by ultrasonic treatment and/or heating to approximately 80° C. for the stated time (Table 1.1) and cooled to room temperature prior to use. A given volume of this solution was divided between several 2 ml chromatography vials, using 0.8–1 ml solution per vial. The head space of each vial was filled with perfluorobutane gas, and the vials were securely capped and shaken for 45 seconds using an Espe CapMix® (mixer for dental materials). The resulting microbubble dispersions were transferred to a larger vial and centrifuged at 2000 rpm for 5 minutes, giving a turbid infranatant below a floating layer of microbubbles. The infranatant was removed by a syringe and replaced with an equal volume of water at neutral pH. The washing step was repeated, but now the infranatant was replaced by 10% (w/w) sucrose. 2 ml portions of the washed dispersion were divided between 10 ml flat-bottomed vials specially designed for lyophilisation,. and the vials were cooled to −47° C. and lyophilised for approximately 48 hours, giving a white fluffy solid substance. The vials were transferred to a vacuum chamber, and air was removed by a vacuum pump and replaced by perfluorobutane gas. Prior to use, water was added and the vials were gently hand-shaken for several seconds, giving microbubble dispersions suitable as ultrasound contrast agents.

The size distribution and volume concentration of the microbubbles were measured using a Coulter Counter Mark II apparatus fitted with a 50 μm aperture with a measuring range of 1–30 μm. 20 μl samples were diluted in 200 ml saline saturated with air at room temperature and allowed to equilibrate for 3 minutes prior to measurement. The measurements were made on microbubble dispersions prior to lyophilisation (washed bubble dispersion) and after lyophilisation (reconstituted with water to the same volume as before lyophilisation). The data is presented in Table 1.2 below.

Figure 1:
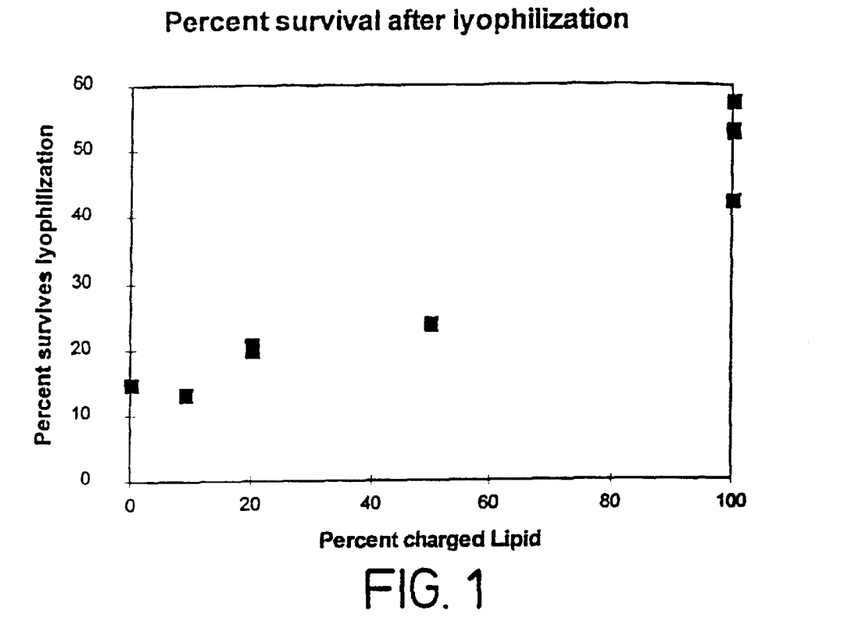
FIG. 1 represents a plot of percentage survival of volume concentration following lyophilisation and reconstitution against relative amount of charged phospholipid in the membranes of contrast agents according to Example 1.

The efficiency of lyophilisation for the different phospholipid stabilised microbubble dispersions was calculated as the percentage survival of the volume concentration following lyophilisation and reconstitution. A plot (see FIG. 1 of the drawings) shows how this parameter varies with the relative amount of charged phospholipid in the membrane. As can be seen, the efficiency of lyophilisation increases with increased amount of charged phospholipid in the membrane, being highest for membranes containing charged phospholipids only.

TABLE 1.1

Composition and process parameters used in production of phospholipid stabilised perfluoro-n-butane gas bubble dispersions as described in Example 1

| PLs and ratios (by weight) | Amount PL [mg/ml] | Amount aqueous solvent [ml] | Sonication bath [min] | Heat treatment [min] | Batch size [ml] | Vol. per vial [ml] |
|---|---|---|---|---|---|---|
| DPPE | 20 | 10 | — | 30 | 10 | 0.8 |
| H-PC/H-PS (9:1) | 45.5 | 9.1 | 10 | 2 | 9 | 0.9 |
| H-PC/H-PS (4:1) | 14.0 | 7 | 10 | 2 | 7 | 1 |
| DSPC/DSPS (4:1) | 10.4 | 5.2 | 10 | 2 | 4 | 1 |
| DSPC/DSPG (1:1) | 15.2 | 7.6 | 10 | 2 | 7 | 1 |
| DPPS | 24.9 | 12.5 | — | 30 | 11 | 1 |
| DSPS | 24.8 | 12.5 | — | 30 | 11 | 1 |
| DSPG/DPPA (10:1) | 20.2 | 10 | — | 10 | 10 | 0.8 |
| DSPG/DPPA (1:1) | 52.0 | 10.4 | — | 10 | 8 | 0.8 |

Legend:
PL = phospholipid
DPPE = dipalmitoylphosphatidylethanolamine
H-PC = hydrogenated egg phosphatidylcholine
H-PS = hydrogenated egg phosphatidylserine
DSPC = distearoylphosphatidylcholine
DSPS = distearoylphosphatidylserine
DSPG = distearoylphosphatidylglycerol
DPPS = dipalmitoylphosphatidylserine
DPPA = dipalmitoylphosphatidic acid.

TABLE 1.2

Yield measured as volume concentration of bubbles (in percent of total dispersion volume) (i) after washing the dispersion and (ii) after lyophilisation and reconstitution

| PLs and ratios (by weight) | % charged lipid in membrane | Vol. conc. (%) prior to lyophilisation | Vol. conc. (%) after lyophilisation | Amount surviving lyophilisation [% initial vol. conc.] |
|---|---|---|---|---|
| DPPE | 0 | 0.7 | 0.1 | 16.4 |
| H-PC/H-PS (9:1) | 10 | 6.4 | 0.9 | 14.1 |

TABLE 1.2-continued

Yield measured as volume concentration of bubbles (in percent of total dispersion volume) (i) after washing the dispersion and (ii) after lyophilisation and reconstitution

| PLs and ratios (by weight) | % charged lipid in membrane | Vol. conc. (%) prior to lyophilis- ation | Vol. conc. (%) after lyophilis- ation | Amount surviving lyophilis- ation [% initial vol. conc.] |
|---|---|---|---|---|
| H-PC/H-PS (4:1) | 20 | 1.0 | 0.2 | 20.0 |
| DSPC/DSPS (4:1) | 20 | 4.8 | 1.0 | 20.8 |
| DSPC/DSPG (1:1) | 50 | 0.3 | 0.1 | 33.3 |
| DPPS | 100 | 0.7 | 0.4 | 57.1 |
| DSPS | 100 | 1.0 | 0.5 | 50.0 |
| DSPG/DPPA (10:1) | 100 | 1.4 | 0.7 | 52.9 |
| DSPG/DPPA (1:1) | 100 | 4.3 | 1.8 | 41.9 |

Legend: See Table 1.1

EXAMPLE 2

Preparation of Perfluorobutane Microbubble Dispersions by Shaking 25.3 mg hydrogenated egg phosphatidylserine was added to 12.5 ml water containing 5.4% (w/w) of a mixture of propylene glycol and glycerol (3:10 w/w). The phospholipid material was hydrated by heating to 70° C. for approximately 30 minutes, followed by cooling to room temperature. 11 ml of the dispersion was divided in 1 ml portions between eleven 2 ml vials, and the head space of the vials was filled with perfluoro-n-butane gas. The vials were securely capped and shaken for 45 seconds using an Espe CapMix® (mixer for dental materials). The resulting microbubble dispersions were combined in four larger vials and centrifuged at 2000 rpm for 5 minutes, giving a turbid infranatant below a floating layer of microbubbles. The infranatant was removed by a syringe and replaced with an equal volume of water at neutral pH. The washing step was repeated, but now the infranatant was replaced by 10% (w/w) sucrose. 2 ml portions of the resulting dispersion were divided between 10 ml flat-bottomed vials specially designed for lyophilisation, and the vials were cooled to −47° C. and lyophilised for approximately 48 hours, giving a white fluffy solid substance. The vials were transferred to a vacuum chamber, and air was removed by a vacuum pump and replaced by perfluoro-n-butane gas. Prior to use, water was added and the vials were gently and-shaken for several seconds, giving microbubble dispersions suitable as ultrasound contrast agents.

b) Preparation of Perfluorobutane Microbubble Dispersions by Rotor Stator Mixing 500.4 mg hydrogenated egg phosphatidylserine was added to 100 ml water containing 5.4% (w/w) of a mixture of propyleneglycol and glycerol (3:10 w/w). The mixture was shaken and heated to 80° C. for five minutes, allowed to cool to room temperature, shaken again and left standing overnight prior to use.

50 ml of the resulting solution was transferred to a round-bottomed flask with a conical neck. The flask was fitted with a glass jacket having a temperature control inlet and outlet connected to a water bath maintained at is 25° C. A rotor stator mixing shaft was introduced into the solution and to avoid gas leakage the space between the neck wall and the mixing shaft was sealed with a specially designed metal plug fitted with a gas inlet/outlet connection for adjustment of gas content and pressure control. The gas outlet was connected to a vacuum pump and the solution was degassed for one minute. An atmosphere of perfluoro-n-butane gas was then applied through the gas inlet.

The solution was homogenised at 23,000 rpm for 10 minutes, keeping the rotor stator mixing shaft such that the openings were slightly above the surface of the liquid. A white coloured creamy dispersion was obtained, which was transferred to a sealable container and flushed with perfluoro-n-butane. The dispersion was then transferred to a separating funnel and centrifuged at 12,000 rpm for 30 minutes, yielding a creamy layer of bubbles at the top and a turbid infranatant. The infranatant was removed and replaced with water. The centrifugation was then repeated twice, but now at 12,000 rpm for 15 minutes. After the last centrifugation, the supernatant was replaced by 10%, (w/w) sucrose. 2 ml portions of the resulting dispersion were divided between 10 ml flat-bottomed vials specially designed for lyophilisation, and the vials were cooled to −47° C. and lyophilised for approximately 48 hours, giving a white fluffy solid substance. The vials were now transferred to a vacuum chamber, and air was removed by a vacuum pump and replaced by perfluoro-n-butane gas. Prior to use, water was added and the vials were gently hand-shaken for several seconds, giving microbubble dispersions suitable as ultrasound contrast agents.

c) Preparation of Perfluorobutane Microbubble Dispersions by Sonication 500.4 mg hydrogenated egg phosphatidylserine was added to 100 ml water containing 5.4% (w/w) of a mixture of propylene glycol and glycerol (3:10 w/w). The mixture was shaken and heated to 80° C. for five minutes, allowed to cool to room temperature, shaken again and left standing overnight prior to use.

This solution was pumped through a 4 ml sonicator flow-through cell and exposed to ultrasound at 20 kHz with an amplitude of 90 μm. The diameter of the sonicator horn was 1.3 cm, the inner diameter of the cell was 2.1 cm and the distance between the horn and the bottom of the cell was 1 cm. The lipid solution was mixed with perfluoro-n-butane at a ratio of 1:2 v/v before it entered the sonicator cell (20 ml/min lipid solution and 40 ml/min perfluoro-n-butane gas). The temperature. was kept at 33° C. A white and creamy dispersion was obtained which was filled into a container and flushed with perfluoro-n-butane.

Characterisation

The size distribution and volume concentration of the microbubbles were measured using a Coulter Counter Mark II apparatus fitted with a 50 μm aperture with a measuring range of 1–30 μm. 20 μl samples were diluted in 200 ml saline saturated with air at room temperature, and allowed to equilibrate for 3 minutes prior to measurement.

Ultrasound characterisation was performed on a experimental set up slightly modified from de Jong, N. and Hoff, L. as described in "Ultrasound scattering properties of Albunex microspheres", Ultrasonics 31(3), pp. 175–181 (1993). This instrumentation measures the ultrasound attenuation efficacy in the frequency range 2–8 MHz of a dilute suspension of contrast agent. During the attenuation measurement a pressure stability test was performed by exposing the sample to an overpressure of 120 mm Hg for 90 seconds. Typically 2–3 μl of sample was diluted in 55 ml Isoton II and the diluted sample suspension was stirred for 3 minutes prior to analysis. As primary response parameter the attenuation at 3.5 MHz was used, together with the recovery attenuation value at 3.5 MHz after release of the overpressure.

TABLE 2.1

In vitro characteristics of bubble dispersions produced according to Example 2(a)–(c) (number and volume weighted concentrations and volume mean diameters, as well as acoustic properties measured according to description above)

| Production method (Example No.) | Number conc. [$10^6$/ ml] | Vol. conc. [%] | Vol. mean diam. [μm] | Atten. at 3.5 Mhz [dB/cm] | Survival after over- pressure [%] | Freq. at max. atten. [MHz] |
|---|---|---|---|---|---|---|
| 2 (a) | 1519 | 1.45 | 3.91 | 30.46 | 100 | 4.1 |
| 2 (b) | 10518 | 6.51 | 3.16 | 150.4 | 96 | 4.3 |
| 2 (c) | 23389 | 9.57 | 3.83 | 117 | 100 | 3.5 |

EXAMPLE 3

Effects of Gas Exchange

The gas contents of five samples prepared according to Example 2(b) above were replaced with air, perfluorobutane, sulphur hexafluoride, trifluoromethylsulphur pentafluoride and tetramethylsilane respectively, according to the following procedure:

Two samples containing lyophilised product from Example 2(b) were placed in a desiccator having a gas inlet and a gas outlet. The desiccator was connected to a Bichi 168 vacuum/distiller controller which permitted controlled evacuation of the samples and inlet of a selected gas. The samples were evacuated at approximately 10 mbar for 5 minutes, whereafter the pressure was increased to atmospheric by inlet of the selected gas, followed by careful capping of the vials. The procedure was repeated using further pairs of samples for each of the selected gases.

2 ml distilled water was added to each vial and the vials were gently hand-shaken prior to use. The resulting microbubble dispersions were characterised with respect to size distribution measurements as described in Example 2. The results are summarised in Table 3.1.

TABLE 3.1

In vitro characteristics of phosphatidylserine- stabilised microbubble dispersions produced according to Example 3 - number and volume weighted concentrations and volume mean diameters

| Gas | Number conc. [$10^6$/ml] | Number mean diam. [μm] | Vol. conc. [%] | Vol. mean diam. [μm] |
|---|---|---|---|---|
| Perfluorobutane | 9756 | 1.8 | 4.9 | 5.8 |
| Trifluoromethyl- sulphur pentafluoride | 10243 | 1.9 | 5.9 | 3.5 |
| Sulphur hexafluoride | 9927 | 1.9 | 5.7 | 3.2 |
| Tetramethylsilane | 9947 | 1.9 | 6.1 | 3.7 |
| Air | 9909 | 1.9 | 6.4 | 4.0 |

As will be seen from the above results there was no significant change in size distribution upon gas exchange.

In vivo Results

One batch prepared with each of the five gases was evaluated in vivo for Doppler enhancement properties at 10 MHz. The dispersions were injected into chinchilla rabbits via an ear vein and measured using a Doppler technique where an ultrasound probe was placed directly on a carotid artery. Signal intensities and duration were recorded and the integral of the Doppler curve was calculated. The results obtained (see Table 3.2 below) showed that microbubbles containing perfluorobutane gave the strongest Doppler intensity enhancement. Microbubbles containing sulphur hexafluoride, trifluoromethylsulphur pentafluoride or tetramethylsilane were only slightly less efficacious as Doppler enhancers than those containing perfluorobutane, giving integrals in the range 60–80% of the figure for perfluorobutane.

TABLE 3.2

Results for i.v. injections of Example 3 products into rabbits (values are adjusted for drift in baseline; the Doppler unit is defined as the increase in Doppler signal relative to that of blood)

| Gas | Integrated Arterial Doppler Enhancement (NDU.s) |
|---|---|
| Perfluorobutane* | 10361 |
| Trifluoromethylsulphur pentafluoride | 6006 |
| Tetramethylsilane | 6370 |
| Sulphur hexafluoride | 6297 |
| Air | 1024 |

*Average of two injections

EXAMPLE 4

Frozen Dispersions and Lyophilised Products 250 mg hydrogenated egg phosphatidylserine was added to 50 ml water for injection containing 5.4% (w/w) of a mixture of propylene glycol and glycerol (7:20 w/w). The mixture was shaken and heated to 80° C. for five minutes, allowed to cool to room temperature, shaken again and left standing overnight prior to use.

100 ml of the resulting solution was transferred to a round-bottomed flask with a conical neck and processed according to the procedure described in Example 2(b). A white coloured creamy dispersion was formed. This dispersion was transferred to a separating funnel and centrifuged at 12,000 rpm for 30 minutes, yielding a creamy layer of microbubbles at the top and a turbid infranatant. The infranatant was removed and replaced with 50 ml water for injection. The centrifugation was then repeated twice, but now at 12,000 rpm for 15 minutes. To 6 ml of the resulting dispersion was added 6 ml 30% (w/w) trehalose; 2 ml portions of this dispersion were divided between 10 ml flat-bottomed vials specially designed for lyophilisation, and the vials were cooled to −47° C. and stored at this temperature for one day.

Half of the vials were thawed after one day at −47° C., giving homogeneous creamy white dispersions of gas microbubbles suitable as ultrasound contrast agents. The thawed dispersions were characterised by measuring size distribution as described in Example 2 above (see Table 4.1). The remaining vials were lyophilised for approximately 48 hours, giving a white fluffy solid substance. The vials were transferred to a vacuum chamber, and air was removed by a vacuum pump and replaced by perfluoro-n-butane gas. Prior to use, water was added and the vials were gently hand-shaken for several seconds, giving bubble dispersions suitable as ultrasound contrast agents. The reconstituted products were characterised by measuring size distribution and acoustic attenuation using the methods as described in Example 2 above. The results are presented in Table 4.1.

TABLE 4.1

Bubble concentration, size data and acoustic data of perfluoro-n-butane gas bubble dispersions stabilised by hydrogenated phosphatidylserine, treated by freeze - thawing and lyophilisation

| Sample treatment | Number conc. [$10^6$/ml] | Vol. conc. [%] | Vol. mean diam. [$\mu$m] | Atten. at 3.5 Mhz [dB/cm] | Survival after over-pressure [%] | Freq. at max. atten. [MHz] |
|---|---|---|---|---|---|---|
| Washed | 10390 | 10.4 | 3.2 | n.a. | n.a. | n.a. |
| Freeze-thawed | 10142 | 9.9 | 3.6 | n.a. | n.a. | n.a. |
| Lyophilised | 7780 | 4.6 | 3.1 | 58.0 | 89 | 5.3 |

Legend:
n.a. = not analysed

EXAMPLE 5

Exposure of Perfluorobutane Microbubble Dispersion to Air-saturated Fluid

A vial containing lyophilised material under an atmosphere of perfluorobutane was prepared as described in Example 2(b). water was added to the vial just before use to give a microbubble dispersion.

200 ml Isoton II fluid was exposed to air for several days at room temperature to give a fully air-saturated solution. Another 200 ml of the fluid was degassed in a vacuum flask at 60° C. for one hour and cooled to room temperature while maintaining the vacuum. Air was admitted to the flask immediately prior to use.

10 $\mu$l portions of the microbubble suspension were added to each of the fluids and the resulting mixtures were incubated for 5 minutes prior to size characterisation (Coulter Multisizer Mark II).

In the degassed environment, where no diffusion of gases from the fluid into the microbubbles would be expected, the mean microbubble diameter was 1.77 $\mu$m and 0.25% of the microbubbles were larger than 5m. In the air-saturated fluid the corresponding values were 2.43 $\mu$m and 0.67%; repeated measurements made after a further 5 minutes indicated that the microbubble sizes had reached a stable value.

These findings show that the average diameter of the microbubbles increased by only 37% when they were exposed to an air-saturated fluid analogous to arterial blood, with very few microbubbles reaching a size which might cause blockage of capillary blood vessels. This may be contrasted with the doubling in size of air/perfluorohexane-containing microbubbles in a similar environment (i.e. a highly diluted dispersion of microbubbles in water containing dissolved air) reported in Example II of WO-A-9503835.

EXAMPLE 6

Pressure Stability of Perfluorobutane Microbubble Dispersion

Vials containing lyophilised material under an atmosphere of perfluorobutane were prepared as described in Example 2(a). Water (2 ml) was added to the vials just before use to give microbubble dispersions.

Figure 2:
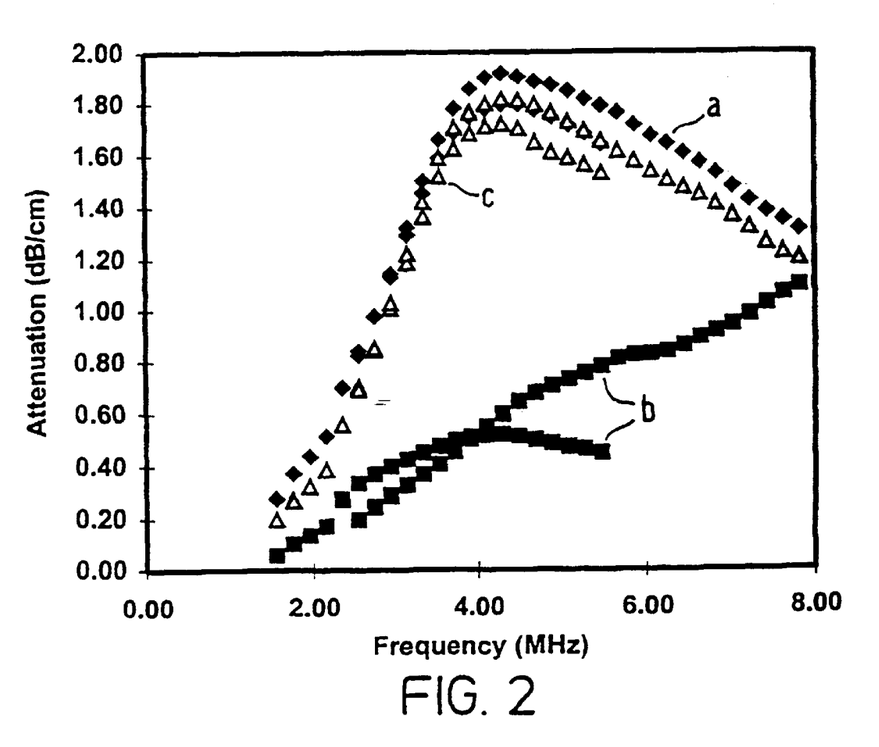
FIG. 2 represents plots of attenuation spectra for the frequency range 1.5–8 MHz of contrast agent according to Example 2(a) measured a) before pressure testing, b) during pressure testing, and c) after pressure testing, as described in Example 6.

Attenuation spectra were recorded for 1.5–8 MHz before, during and after application of an overpressure of air at 300 mm Hg; the pressure was released after 90 seconds. The results are shown in FIG. 2 of the drawings, and indicate that although attenuation at 4 MHz (the peak for unpressurised contrast agent) fell to less than one third under pressure, it was almost fully (85%–95%) restored when the pressure was released.

Figure 3:
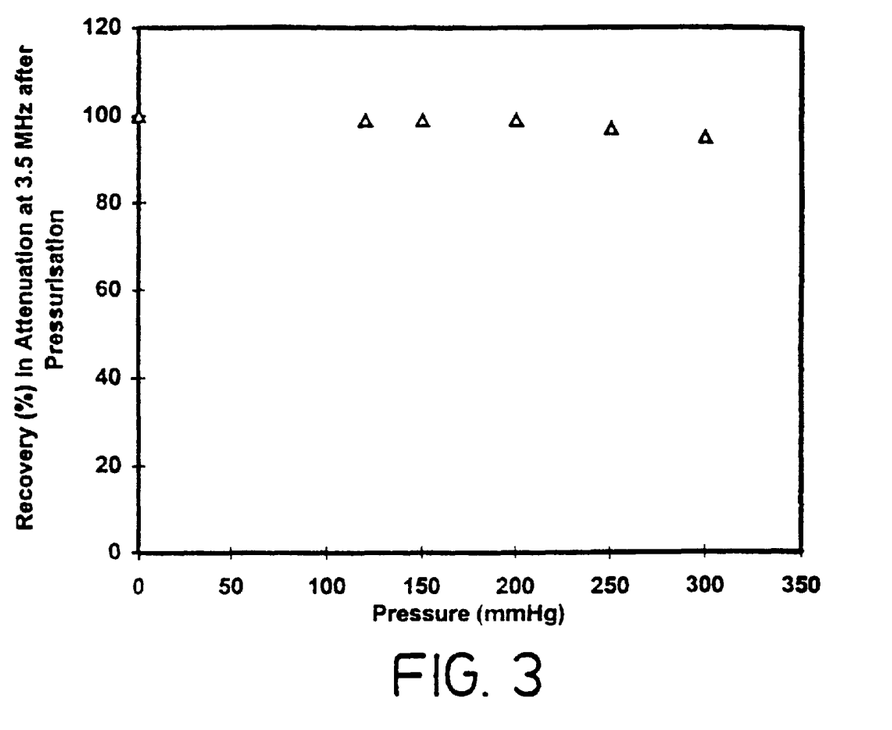
FIG. 3 shows the percentage recovery in attenuation at 3.5 MRz of contrast agent according to Example 2(a) following 90 second applications of overpressures of 0–300mm Hg as described in Example 6.

Overpressures of air at up to 300 mm Hg were applied for 90 seconds duration and attenuation was measured at 3.5 MHz. The results are shown in FIG. 3 of the drawings and indicate good recovery of attenuation (at least about 95%) following pressure release for all the overpressures used.

Figure 4:
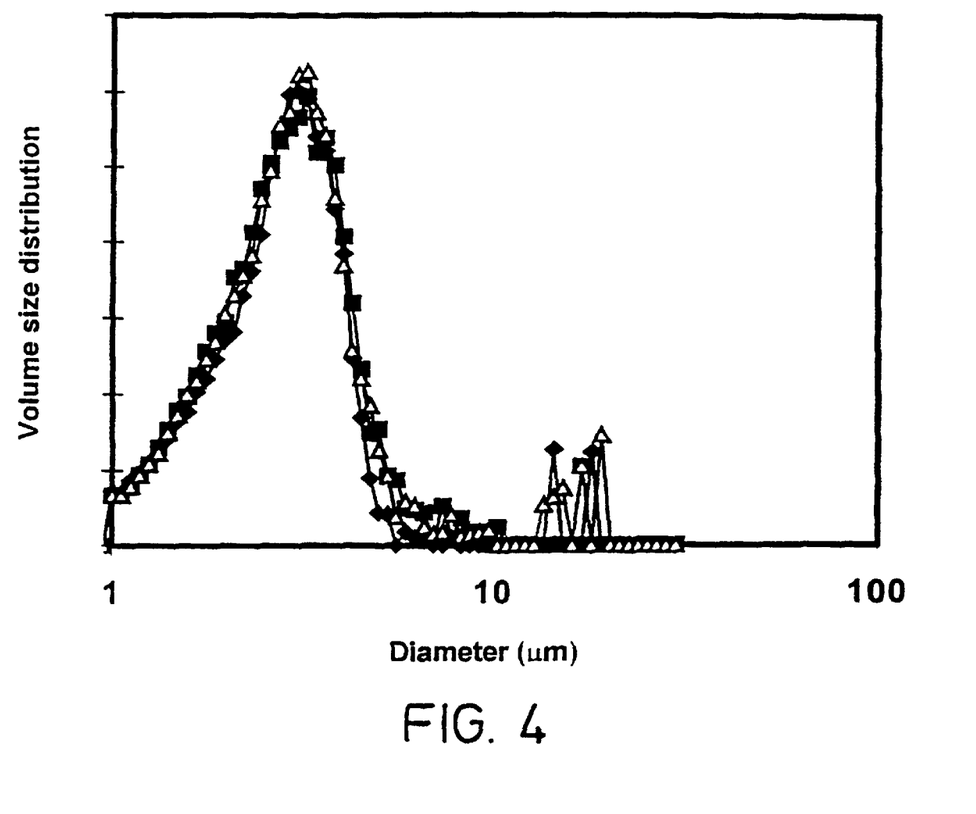
FIG. 4 shows volume size distributions for contrast agent according to Example 2(a) measured by Coulter analysis a) without application of overpressure (♦), b) after 90 seconds of overpressure at 150 mm Hg (Δ), and c) after 90 seconds of overpressure at 300 mm Hg (■), as described in Example 6.

Size distributions were determined by Coulter analysis for a non-pressurised sample and for samples subjected to overpressures of air at 150 and 300 mm Hg applied for durations of 90 seconds. The results are shown in FIG. 4 of the drawings and indicate that there were no significant differences between the distribution curves in the range 1–10 $\mu$m.

What is claimed is:

1. A dispersion of gas microbubbles in an aqueous carrier liquid, said dispersion being stabilised by monolayers of amphiphilic phospholipid material which surround said microbubbles at their interfaces with said carrier liquid, wherein substantially all of the phospholipid consists of molecules which individually have an overall net negative charge, and wherein one or more saturated phosphatidylserines constitute at least 70% of the phospholipid.

2. A microbubble dispersion according to claim 1 wherein the gas is selected from sulphur hexafluoride, perfluorinated low molecular weight hydrocarbons and mixtures of perfluorinated low molecular weight hydrocarbons with nitrogen or air.

3. A microbubble dispersion according to claim 2 wherein the gas is perfluorobutane.

4. An ultrasound contrast agent for use in diagnostic studies, comprising a microbubble dispersion as claimed in claim 1 wherein said aqueous carrier liquid is an injectable aqueous carrier liquid.

5. A lyophilised residue of a microbubble dispersion as claimed in claim 1.

6. A method of diagnostic ultrasound imaging which comprises administering to a subject a contrast-enhancing amount of an ultrasound contrast agent as claimed in claim 4 and generating an ultrasound image of at least a part of said subject.

* * * * *